United States Patent
Gregg (10) Patent No.: US 11,744,502 B2
(45) Date of Patent: Sep. 5, 2023

(54) AUTOMATED DETECTION OF PATIENT AGE BY ECG

(71) Applicant: KONINKLIJKE PHILIPS N.V., Eindhoven (NL)

(72) Inventor: Richard E Gregg, Andover, MA (US)

(73) Assignee: Koninklijke Philips N.V., Eindhoven (NL)

(*) Notice: Subject to any disclaimer, the term of this patent is extended or adjusted under 35 U.S.C. 154(b) by 366 days.

(21) Appl. No.: 15/039,975

(22) PCT Filed: Nov. 26, 2014

(86) PCT No.: PCT/IB2014/066348
§ 371 (c)(1),
(2) Date: May 27, 2016

(87) PCT Pub. No.: WO2015/079387
PCT Pub. Date: Jun. 4, 2015

(65) Prior Publication Data
US 2017/0000366 A1  Jan. 5, 2017

Related U.S. Application Data

(60) Provisional application No. 61/910,350, filed on Nov. 30, 2013.

(51) Int. Cl.
*A61B 5/349* (2021.01)
*A61B 5/00* (2006.01)
(Continued)

(52) U.S. Cl.
CPC .............. *A61B 5/349* (2021.01); *A61B 5/332* (2021.01); *A61B 5/7264* (2013.01); *A61B 5/742* (2013.01);
(Continued)

(58) Field of Classification Search
CPC .... A61B 5/0402; A61B 5/0452; A61B 5/0456
See application file for complete search history.

(56) References Cited

U.S. PATENT DOCUMENTS 6,132,381 A * 10/2000 Forbes ................. A61B 5/0452
                                                      600/483
7,678,049 B2    3/2010 Tsoref et al.
(Continued)

FOREIGN PATENT DOCUMENTS

| JP | 2010162069 | * | 7/2010 |
| JP | 2010162069 A | | 7/2010 |
| WO | 2006059190 A3 | | 2/2008 |

OTHER PUBLICATIONS

Wiggins et al. "Evolving a Bayesian Classifier for ECG-based Age Classification in Medical Applications". Appl Soft Comput. Jan. 2008 ; 8(1): 599-608. doi:10.1016/j.asoc.2007.03.009.*
(Continued)

*Primary Examiner* — Allen Porter (57) ABSTRACT

An automated age detection system employing a patient monitoring lead assembly and a patent monitoring device. In operation, the patient monitoring lead assembly conducts electrical activity of a heart of a patient to the patient monitoring device. In response thereto, the patient monitoring device classifying the patient as an adult patient or a pediatric patient as a function of electrocardiogram feature(s) derived from electrocardiogram measurement(s) of the electrical heart activity. The patient monitoring device may further estimate the age as a function of electrocardiogram feature(s). The classification facilitates an appropriate application of an adult analysis or a pediatric analysis of the electrical heart activity.

20 Claims, 8 Drawing Sheets

(51) Int. Cl.
*A61N 1/39* (2006.01)
*A61B 5/332* (2021.01)

(52) U.S. Cl.
CPC .......... *A61B 5/7405* (2013.01); *A61N 1/3937* (2013.01); *A61B 5/7271* (2013.01)

(56) References Cited

U.S. PATENT DOCUMENTS

| | | | |
|---|---|---|---|
| 8,126,526 | B2 | 2/2012 | Kitajima et al. |
| 8,738,130 | B2 | 5/2014 | Freeman et al. |
| 9,750,449 | B2 | 9/2017 | Stamatas et al. |
| 2003/0019556 | A1 | 1/2003 | Girard et al. |
| 2003/0065264 | A1 | 4/2003 | Tsoref et al. |
| 2003/0195567 | A1 | 10/2003 | Jayne et al. |
| 2005/0131304 | A1 | 6/2005 | Stamatas et al. |
| 2005/0267536 | A1 | 12/2005 | Freeman |
| 2006/0136744 | A1 | 6/2006 | Lange |
| 2007/0118028 | A1 | 5/2007 | Kitajima et al. |
| 2012/0145152 | A1* | 6/2012 | Lain .................. A61B 5/08 128/204.23 |
| 2013/0041276 | A1 | 2/2013 | Liao et al. |
| 2014/0180144 | A1 | 6/2014 | Chen et al. |

OTHER PUBLICATIONS

Attia et al. "Age and Sex Estimation Using Artificial Intelligence frm Standard 12-Lead ECGs." Circulation: Arrhythmia and Electrophysiologyvol. 12, Issue 9, Sep. 2019 <https://doi.org/10.1161/CIRCEP.119.007284> (Year: 2019).*

Shin, HC, Roth, HR, Gao, M, Lu, L, Xu, Z, Nogues, I, Yao, J, Mollura, D, Summers, RM. Deep convolutional neural networks for computer-aided detection: CNN architectures, dataset characteristics and transfer learning. IEEE Trans Med Imaging. 2016;35: 1285-1298. doi: 10.1109/TMI.2016.2528162 (Year: 2016).*

Kingma, DP, Ba, J. Adam: a method for stochastic optimization. 2014;arXiv:1412.6980. (Year: 2014).*

Hu et al. "Intelligent Sensor Networks: The Integration of Sensor Networks", Signal Processing and Machine Learning, CRC Press 2012.*

Brant A. Rustwick et al., "Abstract 10250: Comparison of Electrocardiographic Characteristics for Automated External Defibrillator Algorithms in Children and Adults", Circulation, vol. 122, No. 21, Suppl. S, (2010), p. A10250.

Dickinson, D.F. "The Normal ECG in CHildhood and Adolescense". Heart (2005); vol. 91, No. 12:1626-1630.

Wiggins, M. et al., "Evolving a Bayesian classifier for ECG-based age classification in medical applications". ScienceDirect, Applied Soft Computing vol. 8, No. 1, Sep. 10, 2007, 599-608.

McFarlane, P.W. et al., "Effects of Age, Sex, and Race on ECG Interval Measurements". Journal of Electrocardiology, vol. 27, Jan. 1, 1994, pp. 14-19.

* cited by examiner

AUTOMATED DETECTION OF PATIENT AGE BY ECG

This application is a national stage application under 35 U.S.C. § 371 of International Application No. PCT/IB2014/066348 filed on Nov. 26, 2014 and published in the English language on Jun. 4, 2015 as International Publication No. WO 2015/079387 A1, which claims priority to U.S. Application No. 61/910,350 filed on Nov. 30, 2013, the entire disclosures of which are incorporated herein by reference.

The present disclosure relates to, e.g., medical instruments and more particularly to electrocardiograph ("ECG") equipment and display/interpretation of ECG signals.

Electrocardiograph equipment (e.g., a 12-lead diagnostic device) generates a report called an electrocardiogram. An electrocardiograph ("ECG") signal is a 10 second snapshot of the electrical activity of the heart, for example. The electrocardiogram or ECG report generally includes, amongst other information, patient demographics and ECG interpretation.

Automated ECG analysis is typically divided into separate adult and pediatric analyses. Patient age (or estimation thereof) is generally required to decide which applies, the adult analysis or the pediatric analysis. It is possible that clinicians or other medical practitioners may not enter an age into the analyzing ECG device, especially in urgent situations when they are rushed, for example. In this case, the device would typically default to the automated adult ECG analysis. However, adult interpretation is not appropriate for pediatric patients because, e.g., the thresholds to decide normal versus abnormal are different.

Accordingly, there exists a need for an automated system to prevent the large interpretation errors inherent with application of adult ECG analysis to pediatric ECG analysis.

The present invention provides a novel and inventive system and method to determine and/or estimate a patient's age or age range and (help) decide if the patient is an adult or a child. Exemplary embodiments of the inventive system and method can be based on parameters calculated from a standard 12-lead ECG. However, as one having ordinary skill in the art shall appreciate in view of the teachings provided herein, certain exemplary embodiments of the of the inventive system and method disclosed herein can be based on parameters calculated from other ECG lead configurations/systems/devices. Exemplary system and method according to the present invention can be used, e.g., to provide an approximate age if no age is manually entered or otherwise provided by a user/practitioner (or otherwise given or obtained).

The exemplary system and method can also suggest to the device user/practitioner that a manually entered age (i.e., a baseline age) should be checked if such age does not match the age determined by the system or method. This suggestion can be provided in the way of, e.g., a visual and/or audio alert, voice prompts, etc. It is also possible that a device comprising and/or implementing an exemplary system and/or method in accordance with the present invention be configured so as to allow the user/practitioner to ignore and/or turn off the alerts and proceed uninterrupted, or it can prompt the user/practitioner to confirm age by manual confirmation (e.g., menu item section, pop-up window button, physical button depression, key depression, etc.) or speaking a voice response to the device. A timeout can also be included that would allow the user/practitioner to proceed if no response/confirmation is provided after a pre-selected amount of time (e.g., 1-5 seconds, 3 seconds).

For example, in accordance with an exemplary embodiment of the present invention, it is possible that the exemplary system and/or method use regression on a large ECG database containing both adult and pediatric ECGs. The output of the regression could either be binary (adult or child) or an estimate of age. The regression inputs can be ECG parameters that are generally known to vary widely with age such as heart rate in sinus rhythm, QRS duration and QRS voltage levels. Using a system or method training approach, the best ECG parameters for the job (e.g., those parameters meeting certain pre-defined thresholds and/or other criteria) can be chosen. The corresponding regression coefficients can then be calculated to determine (an estimation and/or range of) the patient's age. Using a similar training database as mentioned above, a machine learning method for computerized classification could be trained to recognize ECGs which are either pediatric or adult as a binary decision rather than an estimate of the patient's age.

According to certain exemplary embodiments of the present invention, the ECG parameters can be calculated from a standard 12-lead ECG. The patient's age can then be determined and/or estimated by applying an exemplary embodiment of the system and/or method in accordance with the present invention. Once the age is determined and/or estimated, it can be compared to the age as may have been entered or otherwise provided by a user/practitioner (or otherwise given or obtained). If the age is unknown, a default age can be used based on the age as determined and/or estimated by the exemplary system or method.

If the age is known, it can be compared to the age as determined and/or estimated by the exemplary system or method. If the manually entered age and age determined/estimated by the exemplary system or method indicates an adult patient/pediatric patient classification error, the device can indicate to the user that there is a discrepancy (e.g., and that the manually entered age appears to be incorrect). This indication can be provided in the way of, e.g., a visual and/or audio alert, voice prompts, etc. For example, a device comprising and/or implementing an exemplary system and/or method in accordance with the present invention can be configured so as to allow the user/practitioner to ignore and/or turn off the alerts and proceed uninterrupted, or it can prompt the user/practitioner to confirm age by manual confirmation (e.g., menu item section, pop-up window button, physical button depression, key depression, knob (re)selection, switch, etc.) or speaking a voice response to the device/system. A timeout can also be included that would allow the user/practitioner to proceed if no response/confirmation is provided after a set pre-selected amount of time (e.g., 1-5 seconds, 3 seconds).

Exemplary embodiments of the present invention can be integrated/used in/with any Advanced Life Support (ALS) Monitor/Defibrillator as well as Automated External Defibrillators (AEDs) and any other patient monitoring devices which can capture and analyze 12-lead (or other) ECG information. Indeed, while exemplary embodiments of the present invention are described herein with a focus on a 12-lead ECG device, one having ordinary skill in the art shall appreciate in view of the teachings provided herein that exemplary embodiments of the present invention can be applied to any ECG measuring device and/or system, and are specifically contemplated and considered as being within the scope of the present invention.

In one form of the present invention, the system employs a patient monitoring lead assembly and a patient monitoring device. In operation, the patient monitoring lead assembly conducts electrical activity of a heart of the patient to the patient monitoring device. The patient monitoring device classifies an age of the patient as an adult patient (e.g., age >16 years) or a pediatric patient (e.g., age ≤16 years) as a function of ECG feature(s) derived from ECG measurement(s) of the electrical heart activity. If the patient is classified as a pediatric, then the patient monitoring device may further estimate the age of the classified pediatric patient as a function of the ECG feature(s).

The term "patient monitoring lead assembly" is a specific known grouping of lead assemblies including, but not limited to, any 12-lead assembly.

The term "patient monitoring device" is a specific known grouping of devices for monitoring patients including, but not limited, to any Advanced Life Support ("ALS") monitors/defibrillators and any Automated External Defibrillators ("AED").

The term "ECG features" as used in the present application broadly encompasses calculated ECG parameters quantitatively decipherable for distinguishing a pediatric patient from an adult patient. Examples of such ECG parameters identified in an exemplary study subsequently described herein include, but are not limited to, patient heart rate, T-wave amplitude relative to QRS amplitude, QRS peak-to-peak amplitude, biphasic QRS complexes, QRS duration and negative T-waves on leads V2 and V3.

In a second form of the present invention, a controller of the patient monitoring device employs modules in the form of an ECG feature calculator for calculating ECG feature(s) derived from ECG measurement(s) of electrical heart activity, and a patient classifier for classifying the patient as an adult patient (e.g., age >16 years) or a pediatric patient (e.g., age ≤16 years) as a function of the ECG feature calculation(s). The controller may further employ a pediatric age estimator for estimating an age of a patient classified as a pediatric patient.

For purposes of the present invention, the term "controller" broadly encompasses all structural configurations of an application specific main board or an application specific integrated circuit housed within or linked to a patient monitoring device for controlling an application of various inventive principles of the present invention as subsequently described herein. The structural configuration of the controller may include, but is not limited to, processor(s), computer-usable/computer readable storage medium(s), an operating system, peripheral device controller(s), slot(s) and port(s).

For purposes of the present invention, the term "module" broadly encompasses an application component of the controller consisting of an electronic circuit and/or an executable program (e.g., executable software and/or firmware).

The foregoing forms and other forms of the present invention as well as various features and advantages of the present disclosure will become further apparent from the following detailed description of various embodiments of the present disclosure read in conjunction with the accompanying drawings. The detailed description and drawings are merely illustrative of the present invention rather than limiting the scope of the present disclosure being defined by the appended claims and equivalents thereof.

The following is a description of an exemplary study for identifying and processing ECG features for purposes of classifying/estimating an age of a patient.

EXEMPLARY STUDY

Sometimes patient age information is missing from 12-lead ECG (or other ECG) records. In light of this missing information, the present invention recognizes that patient age information can be important and typically critical to correct pediatric ECG interpretation, for example. The present invention further recognizes automated pediatric ECG analysis could benefit from an estimated age rather than defaulting to adult ECG analysis when no age is provided. According to an exemplary embodiment of the present invention, the exemplary system and/or method can first determine if an ECG was a pediatric ECG and if so, then in a second step the pediatric age can be estimated from the ECG.

Exemplary Study Population: The present inventor conducted an exemplary study in which the set was a combination of two sets: adult patients from a teaching hospital (n=990) and pediatric patients from a children's hospital (n=455). More particularly, in the combined database, there were 154 patients with ages from birth to 1 year, 48 patients age 1 to 5, 47 patients 5 to 10, 124 patients 10 to 16, 133 patients 16 to 40, 292 patients 40 to 60 and 647 patients over the age of 60 years.

Exemplary study methods: The present inventor analyzed ECGs of the set via the Philips DXL algorithm for basic parameters like heart rate and QRS duration. ECGs were further processed to generate ECG features particular to pediatric ECGs such as the number of leads with biphasic QRS, average QRS peak-to-trough voltage and ratio of T-wave to R-wave amplitude. The data set was randomly split in half to create test and training sets. Regression analysis was used to select the best ECG features and regression coefficients to partition the training set according to the age groups. The trained regression model was then applied to predict the age group of the ECGs in the test set. Performance of the age group classification was measured on the test set by sensitivity and specificity of picking the right age group, age ≤16 years for pediatric patients or age >16 years for adult patients. A second linear regression model was used to estimate age in the pediatric group. Performance of the pediatric age estimation in the test set was measured by correlation coefficient and RMS error.

Exemplary Study Results: ECGs of the test set were separated into age groups age ≤16 years (positive event) and age >16 years (negative event) with a sensitivity of 40% and a specificity of 99.4%. The age estimate in the test set pediatric group had an RMS error of 3.2 years and a correlation coefficient of 0.85 compared to the true age.

Exemplary Study Conclusion: Pediatric age group can be determined with high specificity from ECG features alone. In addition, pediatric age can be estimated from ECG features with good accuracy. High specificity is most important because it means the chance of classifying a true pediatric ECG as adult and using adult analysis on a pediatric ECG is very low.

All of the methods and systems of the present invention are premised on the conclusion of the exemplary study.

To facilitate an understanding of the present invention, exemplary embodiments of the present invention will be provided herein directed to an integration of a controller 20 (FIG. 2) of a patient monitor device 10 (FIG. 1) in the form of a commercially available HeartStart MRx Monitor/Defibrillator. Controller 20 aids a user of patient monitor device 10 in implementing a pediatric ECG analysis or an adult ECG analysis based on a classified/estimated age of the patient. From description of the exemplary embodiments as shown in FIGS. 1-8, those having ordinary skill in the art will appreciate how to make and use the present invention for implementation by/integration into any patient monitoring device known in the art prior to or subsequent to the present invention (e.g., any ALS monitor/defibrillator and any AED).

Figure 1A:
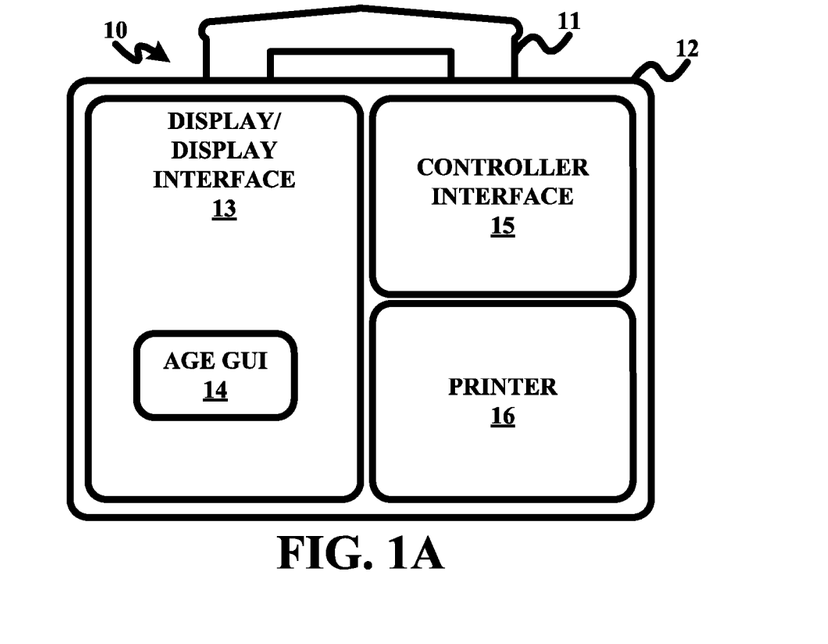
FIGS. 1A and 1B respectively illustrate a front view and a side view of an exemplary portable monitor/defibrillator in accordance with the present invention.
Figure 1B:
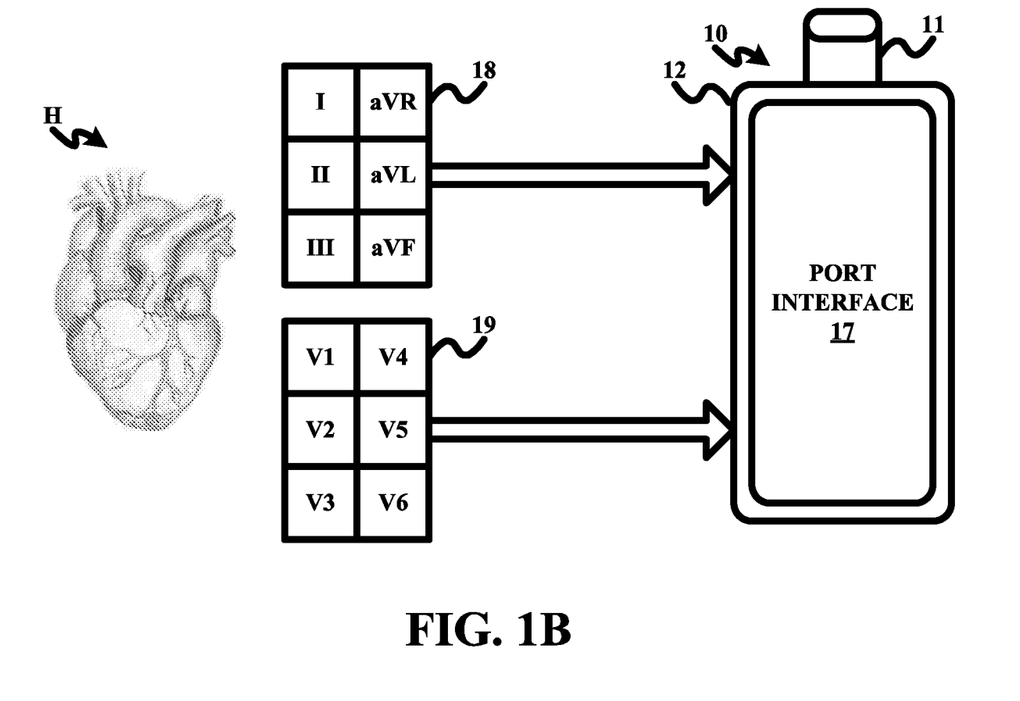
Figure 2:
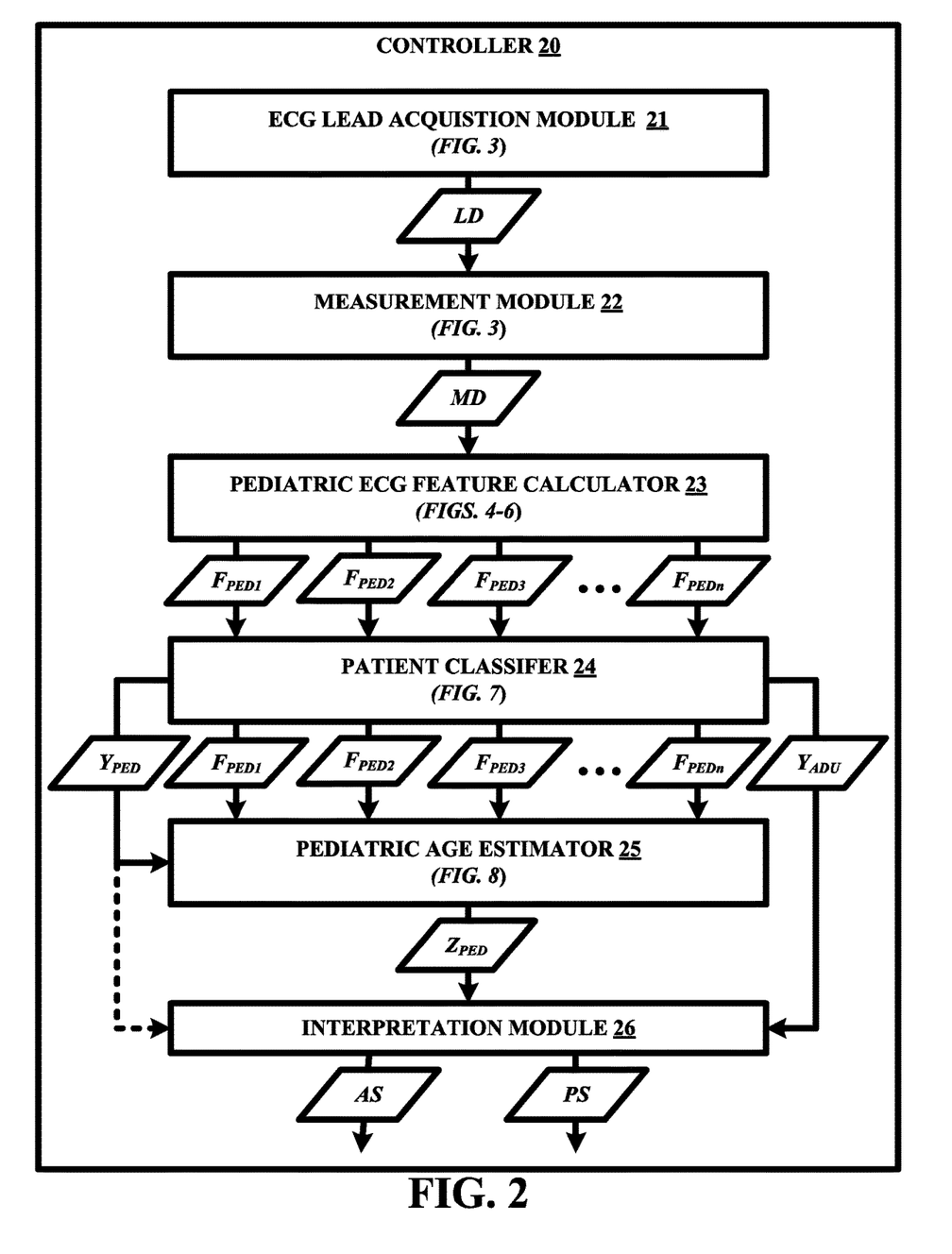
FIG. 2 illustrates a block diagram of an exemplary controller in accordance with the present invention.

Referring to FIGS. 1 and 2, a block diagram of patient monitoring device 10 shows a handle 11 attached to a housing 12 providing user-access to a display/display interface 13, a controller interface 15, a printer 16 and a port interface 17 as shown in FIG. 1. Housing 12 further encloses controller 20 as shown in FIG. 2.

As known in the art:
(1) display/display interface 13 displays patient monitoring data as customized by a user via display interface 13 (e.g., keys);
(2) controller interface 15 (e.g., knobs and buttons) allows the user to apply various therapies (e.g., a shock) to a patient as controlled by controller 20;
(3) printer 16 allows the user to print various patient reports, status logs and device information;
(4) port interface 17 allows for the connection by the user of a patient monitoring lead assembly including limb leads 18 and precordial leads 19 as known in the art; and
(5) controller 20 includes therapy modules (not shown) based on an age of a patient as entered into controller 20 via an age GUI 14.

This exemplary embodiment of the present invention is directed to additional modules 21-26 of controller 20 for classifying/estimating an age of the patient to facilitate an execution of the correct age appropriate therapy modules irrespective of the age entered into controller 20.

For purposes of the present invention, the terms of the art including, but not limited to, terms associated with a generation and an analysis of an ECG report, are to be interpreted as known in the art of the present invention.

Figure 3:
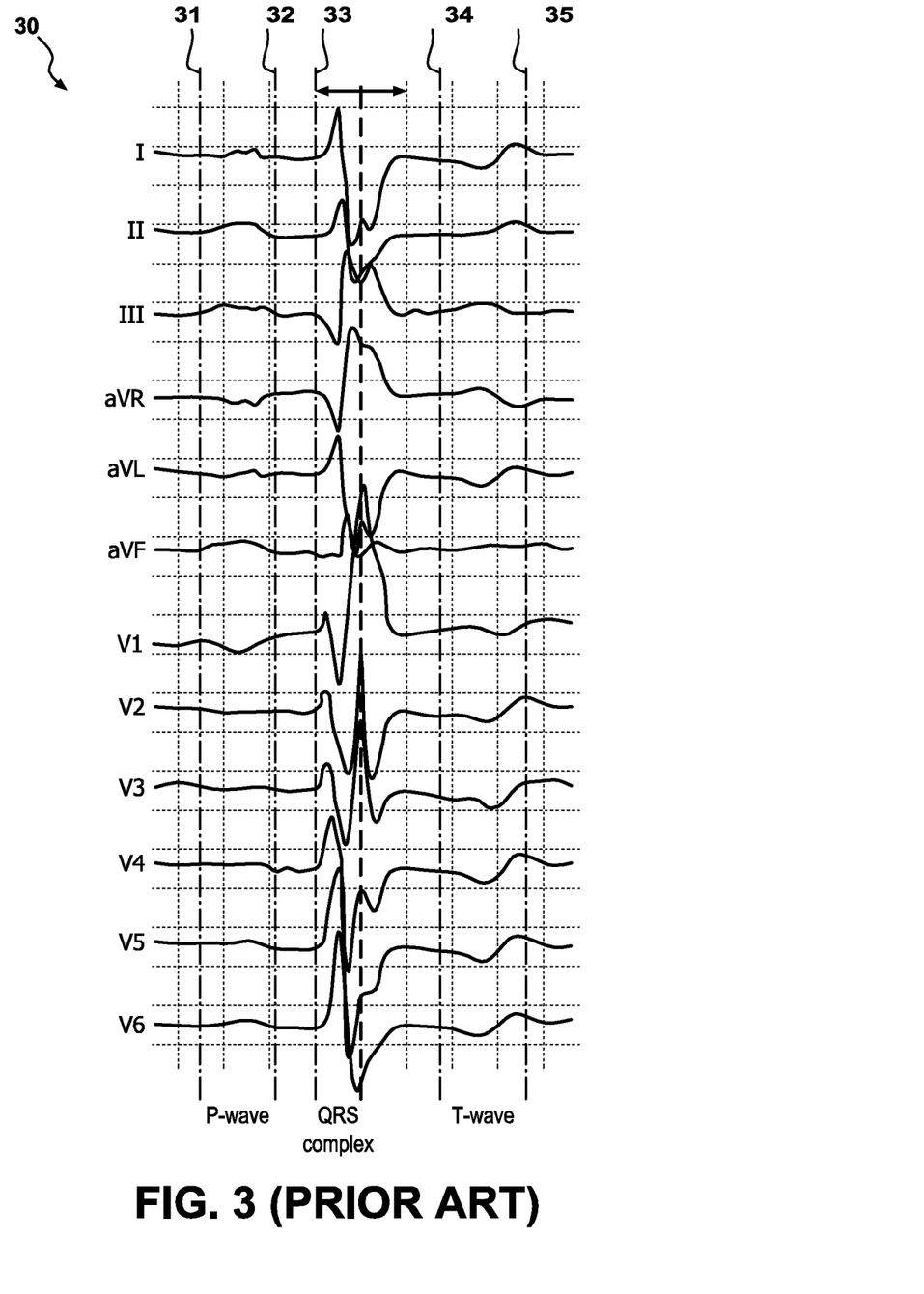
FIG. 3 illustrates an exemplary electrocardiogram in the form of a single heart beat as known in the art to demonstrate the present inventive principles.

Referring to FIG. 2, an ECG lead acquisition module 21 is structurally configured as known in the art to acquire electrical heart activity from leads 18/19 as connected to port interface 17. For example, FIG. 3 illustrates an exemplary electrocardiogram 30 representative of lead acquisition of electrical heart activity. In practice, more or less leads 18/19, or different leads than leads 18/19 may be utilized to acquire the electrical heart activity.

Referring back to FIG. 2, in response to lead data LD from module 21 informative of the electrical heart activity, a measurement module 22 is structurally configured as known in the art to execute various ECG measurements of the electrical heart activity including, but not limited to, an average beat, global measurements and lead by lead measurements. For example, FIG. 3 illustrates exemplary fiducial markers 31-35 for global measurements including PR interval, QRS duration and QT interval of the electrical heart activity. In practice, module 22 will execute measurements corresponding to a calculation of ECG features as further described herein.

Referring back to FIG. 2, in response to measurement data MD from module 22 informative of the ECG measurements, ECG feature calculator 23 calculates a n number of ECG features, n≥1. The calculated ECG features facilitate distinction between a pediatric patient and an adult patient.

Figure 4:
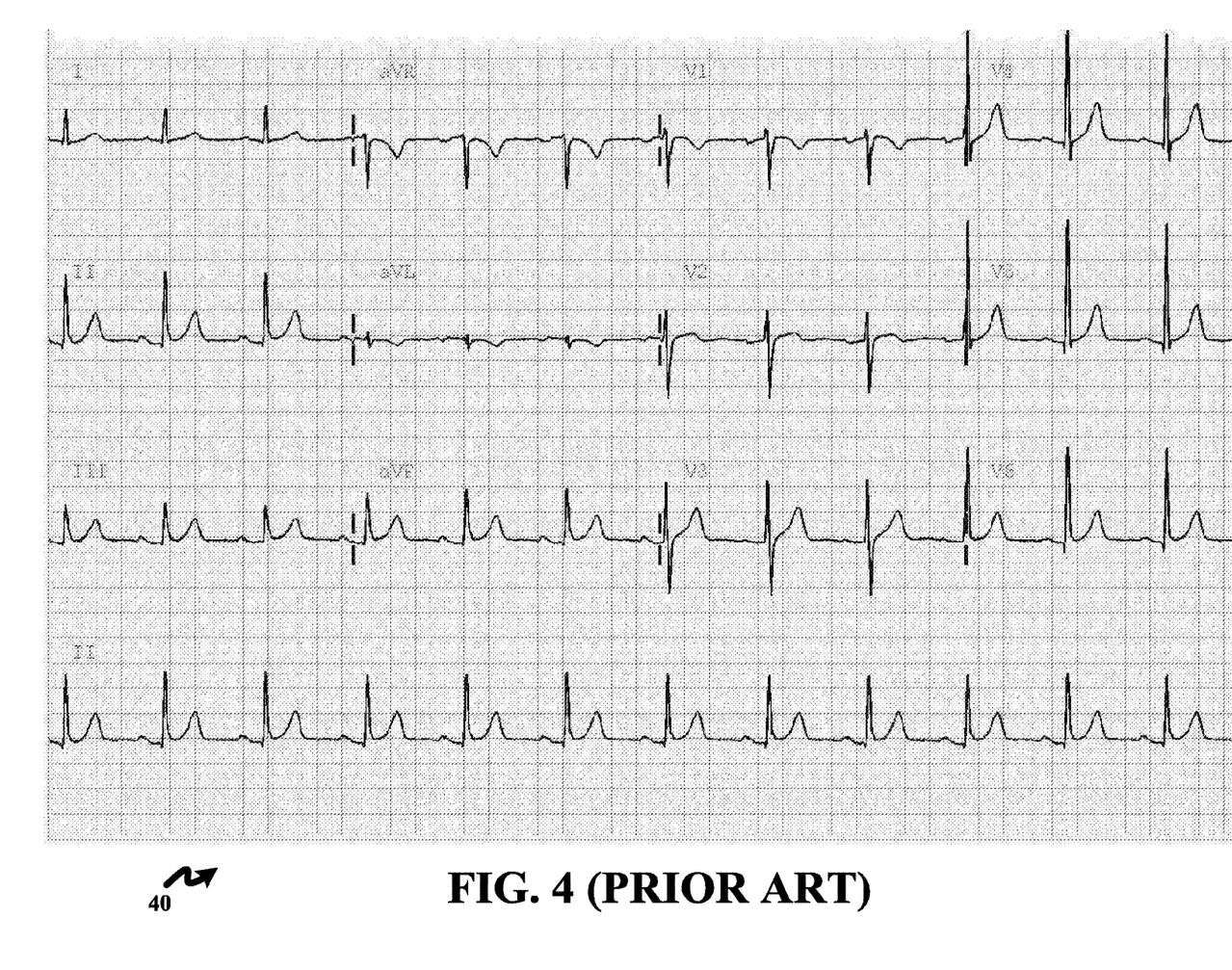
FIG. 4 illustrates an exemplary ten second 12-lead ECG report for an adult patient as known in the art to demonstrate the present inventive principles.
Figure 5:
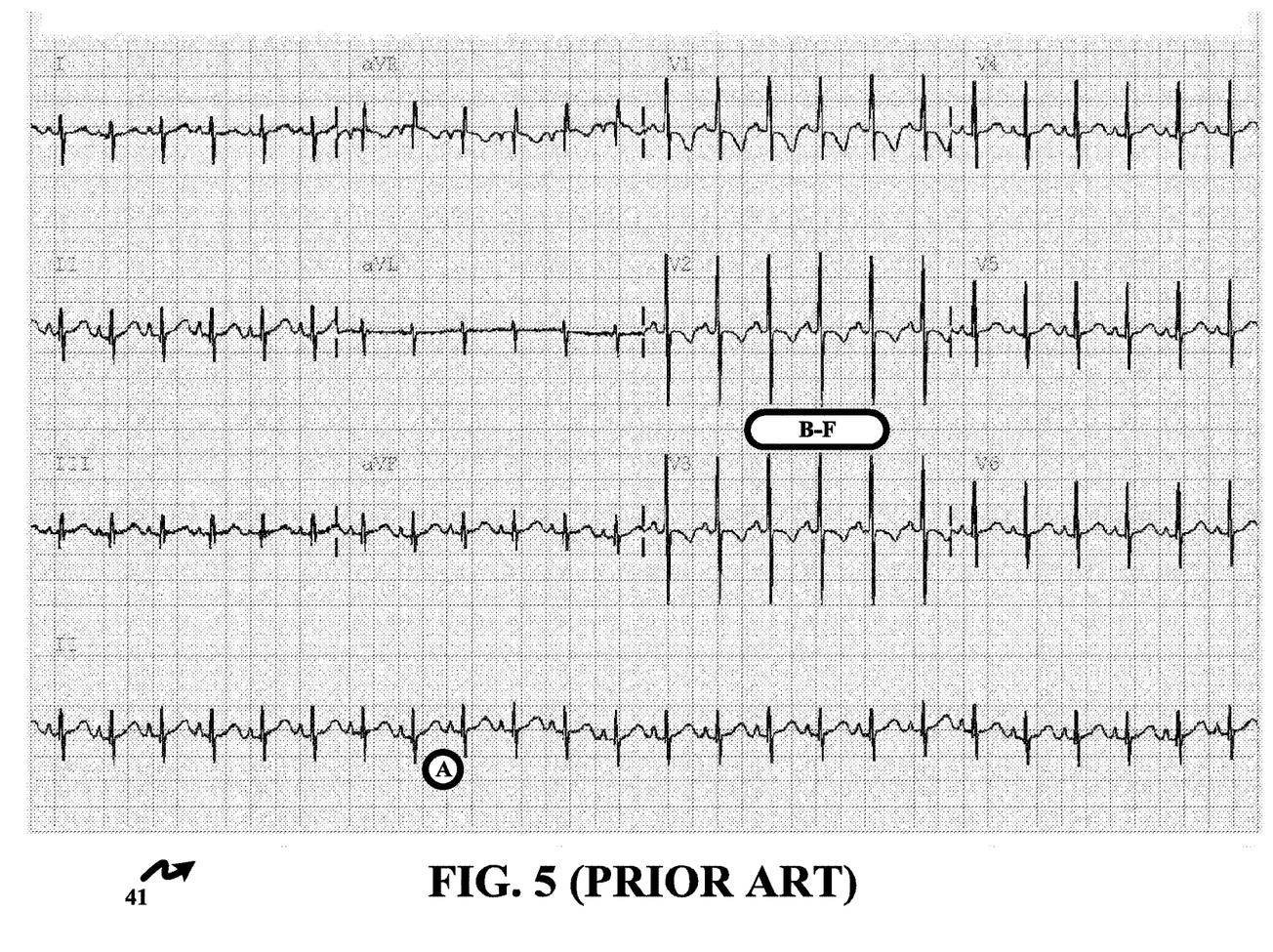
FIG. 5 illustrates an exemplary ten second 12-lead ECG report for a pediatric patient as known in the art to demonstrate the present inventive principles.

For example, FIG. 4 illustrates a 12-lead ECG report 40 for an adult patient and FIG. 5 illustrates a 12-lead ECG report 41 for a pediatric patient. In comparison, report 41 highlights the facts that:
(A) Pediatric patients typically have a higher heart rate;
(B) Pediatric patients typically have a lower T-wave amplitude relative to QRS amplitude;
(C) Pediatric patients typically have a larger QRS peak-to-peak amplitude;
(D) Pediatric patients typically have more leads with highly biphasic QRS complexes;
(E) Pediatric patients typically have a narrower/shorter QRS duration; and
(F) Pediatric patients typically have negative T-waves on leads V2 and V3.

Another example not perceptible in reports 40 and 41 is pediatrics typically have a higher level of sinus arrhythmia (i.e., a RR interval increases and decreases slowly with breathing).

Figure 6:
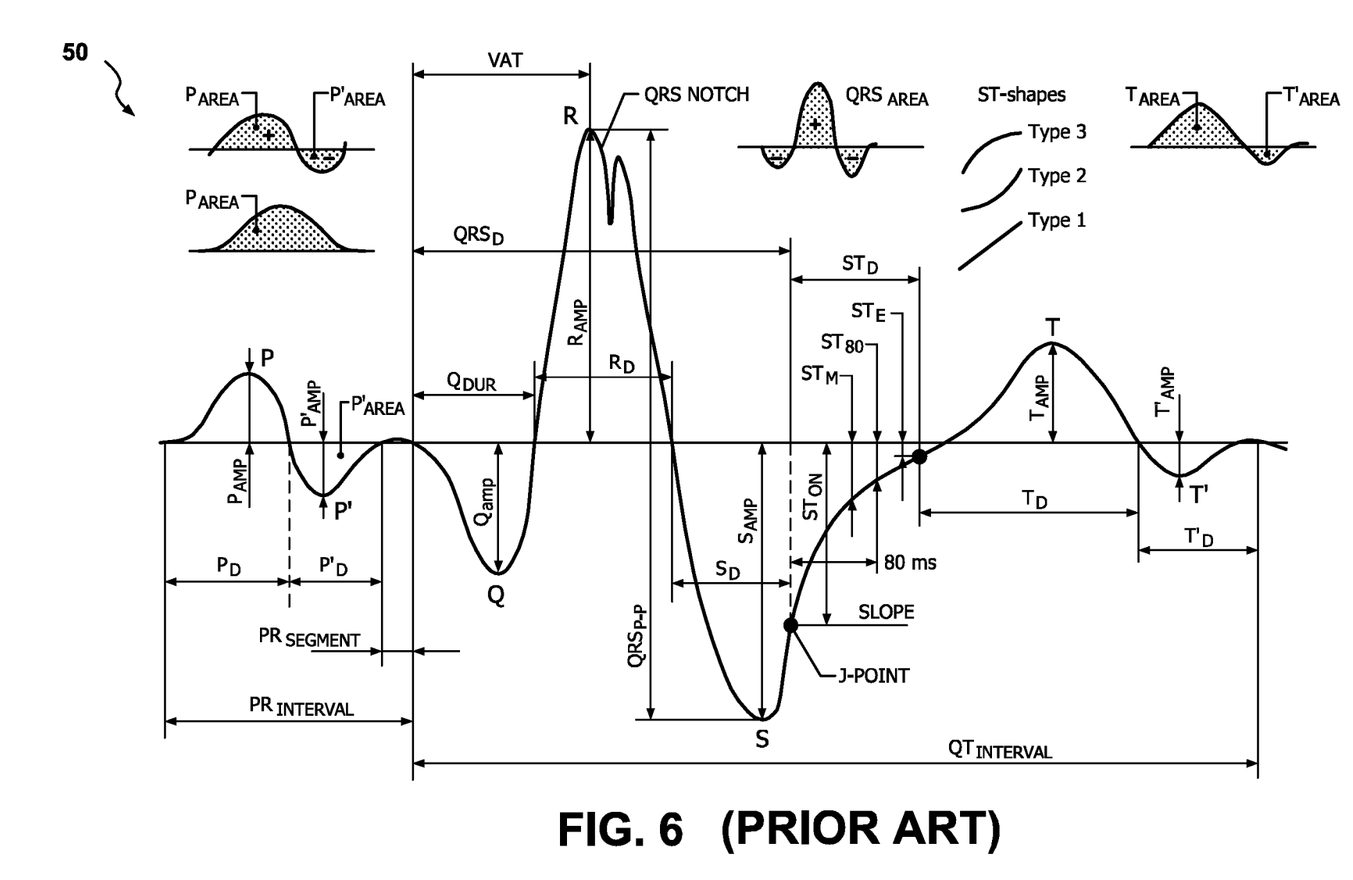
FIG. 6 illustrates an exemplary plot showing ECG calculations as known in the art to demonstrate the present inventive principles.

ECG feature calculator 23 will calculate the n designated ECG features in accordance with known calculation techniques, such as, for example, calculations 50 shown in FIG. 6 (for which an explanation is not necessary). Those having ordinary skill in the art will appreciate further calculations may be performed as necessary in feature calculator 23 to provide numerical measures of the types of age dependent differences noted between FIGS. 4 and 5.

Referring back to FIG. 2, in response to calculated pediatric data $F_{PED}$ informative of the calculated ECG features, a patient classifier 24 generates a pediatric classification $Y_{PED}$ or an adult classification $Y_{ADU}$ derived from an execution of a function on calculated feature data $F_{PED}$ that explicitly delineates a summation of features $F_{PED}$ as identifying a pediatric patient or an adult patient.

Figure 7:
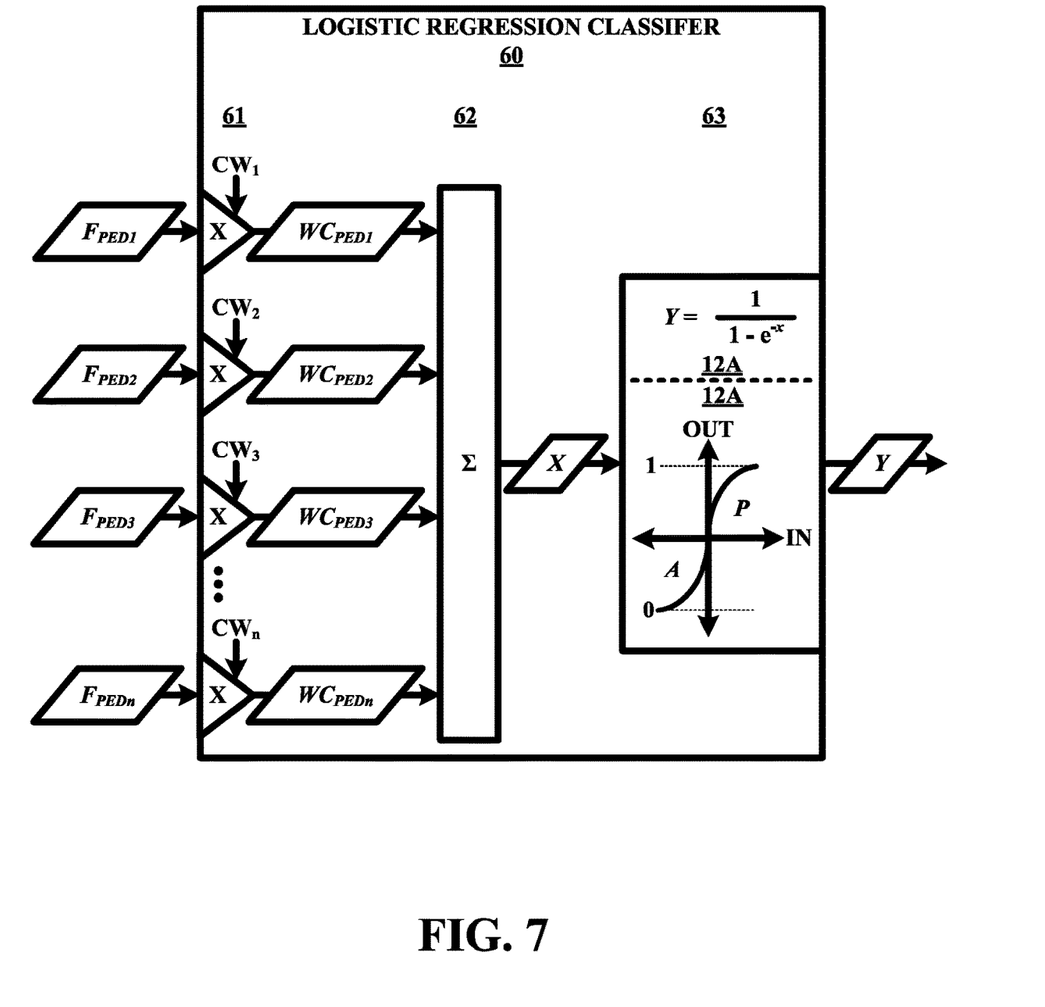
FIG. 7 illustrates an exemplary embodiment of a patient classifier in accordance with the present invention.

FIG. 7 illustrates a logistic regression embodiment 60 of patient classifier 24. Logistic regression classifier 60 involve three (3) stages including:
(1) a multiplication stage 61 whereby each calculated ECG feature $F_{PED}$ is multiplied by a classification weight CW derived from training/testing as previously described herein to yield a weighted classification contribution $WC_{PED}$;
(2) a summer stage 62 whereby each weighted classification contribution $WC_{PED}$ is added to yield a patient classification X; and
(3) a normalized output stage 63 whereby patient classification X is converted to a normalized classification Y indicative of an adult patient classification if $Y_{ADU}<0.5$ (e.g., age >16 years) or a pediatric patient classification if $Y_{PED}\geq0.5$ (e.g., age ≤16).

Referring back to FIG. 2, if normalized classification Y indicates an adult patient classification $Y_{ADU}$, then an interpretation module 26 generates adult ECG interpretation statement(s) AS. In addition, the user is informed that the therapy modules will be executed under an adult mode.

Otherwise, if normalized classification Y indicates a pediatric patient classification $Y_{PED}$, then pediatric age estimator 25 estimates a pediatric age $Z_{PED}$ derived from an execution of a function on calculated ECG feature data $F_{PED}$ that approximates an age of the pediatric patient.

Figure 8:
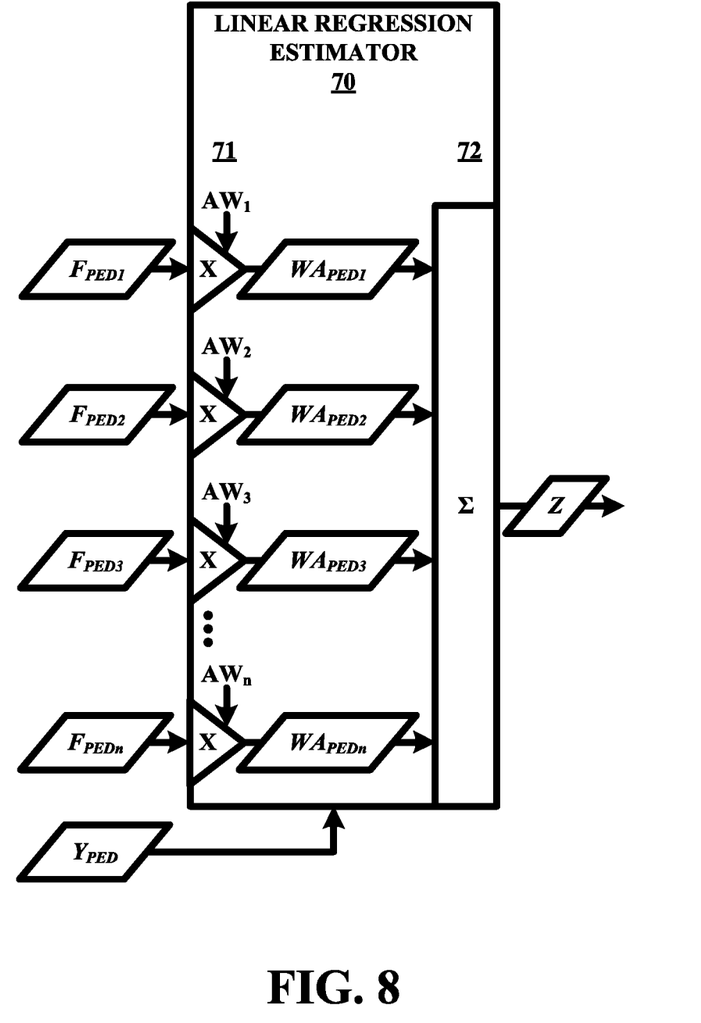
FIG. 8 illustrates an exemplary embodiment of a pediatric age estimator in accordance with the present invention.

FIG. 8 illustrates an linear regression embodiment 70 of estimator 25. If enabled by pediatric classification $Y_{PED}$, the linear regression estimator 70 involve two (2) stages including:

(1) a multiplication stage 71 whereby each ECG feature $F_{PED}$ is multiplied by an age weight AW derived from training/testing as previously described herein to yield a weighted age contribution $WA_{PED}$; and (2) a summer stage 72 whereby each weighted age contribution $WA_{PED}$ is added to yield an estimated pediatric age Z.

Referring back to FIG. 2, in response to pediatric age $Z_{PED}$ informative of the estimated pediatric age, interpretation module 26 generates pediatric ECG interpretation statement(s) PS. The user is informed that the therapy modules will be executed under a pediatric mode. This is especially important if an adult age was mistakenly entered into controller 20 or assumed by default.

Alternatively, pediatric age estimator 25 may be omitted whereby in response to pediatric patient classification $Y_{PED}$ informative of the pediatric patient classification (as indicated by the dashed line), interpretation module 26 generates pediatric ECG interpretation statement(s) PS and the user/operator is informed that the therapy modules will be executed under a pediatric mode. Again, this is especially important if an adult age was mistakenly entered into controller 20 or assumed by default.

Referring to FIGS. 1 and 2, if an age to the patient has been entered into device 10 or otherwise provided, controller 20 may compare estimated pediatric age $Z_{PED}$ to entered/provided age of patient 10 (i.e., a baseline patient age). If the comparison estimated pediatric age $Z_{PED}$ to the baseline patient age of patient 10 indicates an adult patient/pediatric patient classification error, the controller 20 indicates to the user that there is a discrepancy (e.g., and that the manually entered age appears to be incorrect). In practice, controller 20 may provide this indication in numerous way including, but not limited to, a visual and/or audio alert, voice prompt(s), etc. Furthermore, controller 20 may allow the user/practitioner to ignore and/or turn off the alerts and proceed uninterrupted, or controller 20 may prompt the user/practitioner to confirm age by manual confirmation (e.g., menu item section, pop-up window button, physical button depression, key depression, knob (re)selection, switch, etc.) or speaking a voice response to the device/system. Controller 20 may also implement a timeout that would allow the user/practitioner to proceed if no response/confirmation is provided after a set pre-selected amount of time (e.g., 1-5 seconds, 3 seconds).

Additionally, if no age of the patient has been entered into device 10 or otherwise provided, controller 20 may compare patient classification Y or estimated pediatric age $Z_{PED}$ to a baseline adult classification. If the comparison of patient classification Y or estimated pediatric age $Z_{PED}$ to the baseline adult classification indicates an adult patient/pediatric patient classification error, the controller 20 indicates to the user that there is a discrepancy. Similar to the age-to-age comparison, in practice, controller 20 may provide this indication in numerous way including, but not limited to, a visual and/or audio alert, voice prompt(s), etc. Furthermore, controller 20 may allow the user/practitioner to ignore and/or turn off the alerts and proceed uninterrupted, or controller 20 may prompt the user/practitioner to confirm the class by manual confirmation (e.g., menu item section, pop-up window button, physical button depression, key depression, knob (re)selection, switch, etc.) or speaking a voice response to the device/system. Controller 20 may also implement a timeout that would allow the user/practitioner to proceed if no response/confirmation is provided after a set pre-selected amount of time (e.g., 1-5 seconds, 3 seconds).

Referring to FIGS. 1-8, those having ordinary skill in the art will appreciate numerous benefits and advantages of the present invention including, but not limited to, methods and systems to impede, if not prevent, large interpretation errors inherent with application of adult ECG analysis for a pediatric patient.

Further, as one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method to determine and/or estimate a patient's age and whether the patient is adult or pediatric (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An automated age detection system, comprising:
   a patient monitoring lead assembly and a patient monitoring device;
   wherein the patient monitoring lead assembly is operable in communication with the patient monitoring device to conduct electrical activity of a heart of a patient to the patient monitoring device;
   wherein, responsive to the electrical activity of the heart of the patient, the patient monitoring device is configured to calculate at least two electrocardiogram features from an electrocardiogram measurement of at least one heartbeat of the patient; and
   wherein the patient monitoring device is further configured to classify the patient as an adult patient or a pediatric patient based on a regression analysis of a summation of a calculated at least two electrocardiogram features.

2. The automated age detection system of claim 1,
   wherein the patient monitoring device is further configured to apply an adult analysis of the electrical activity of the patient responsive to a classification of the patient as an adult patient; and
   wherein the patient monitoring device is further configured to apply a pediatric analysis of the electrical activity of the heart responsive to classification of the patient as a pediatric patient.

3. The automated age detection system of claim 1, wherein at least one of:
   (i) the patient monitoring device is further operable to apply an adult analysis of the electrical activity of the patient responsive to a classification of the patient as an adult patient, or
   (ii) the patient monitoring device is further configured to apply a pediatric analysis of the electrical activity of the heart responsive to a classification of the patient as a pediatric patient.

4. The automated age detection system of claim 1,
   wherein the patient monitoring device includes a baseline adult classification;
   wherein the patient monitoring device is further configured to compare a classification of the patient as the adult patient or the pediatric patient to the baseline adult classification; and
   wherein the patient monitoring device is further configured to identify a discrepancy between the classification of the patient as the adult patient or the pediatric patient and the baseline adult classification.

5. The automated age detection system of claim 1,
   wherein the patient monitoring device is further configured to compare a classification of the patient as the adult patient or the pediatric patient to a baseline age of the patient; and
   wherein the patient monitoring device is further configured to identify a discrepancy between the classification of the patient as the adult patient or the pediatric patient and the baseline age of the patient.

6. The automated age detection system of claim 1, wherein the patient monitoring device is further configured to estimate a pediatric age of the patient responsive to a classification of the patient as an pediatric patient.

7. The automated age detection system of claim 6, wherein the patient monitoring device is further configured to apply a pediatric analysis of the electrical activity of the heart responsive to an estimation of the pediatric age of the patient.

8. The automated age detection system of claim 6,
   wherein the patient monitoring device includes a baseline adult classification;
   wherein the patient monitoring device is further configured to compare an estimation of the pediatric age of the patient to the baseline adult classification; and
   wherein the patient monitoring device is further configured to identify a discrepancy between the estimation of the pediatric age of the patient and the baseline adult classification.

9. The automated age detection system of claim 6,
   wherein the patient monitoring device is further configured to compare an estimation of the pediatric age of the patient to a baseline age of the patient; and
   wherein the patient monitoring device is further configured to identify a discrepancy between an estimation of the pediatric age of the patient and the baseline age of the patient.

10. The automated age detection system of claim 1, wherein the at least two electrocardiogram features includes at least two of:
- a patient heart rate;
- a T-wave amplitude relative to a QRS amplitude;
- a QRS peak-to-peak amplitude;
- a biphasic QRS complex;
- a QRS duration; and
- at least one negative T-wave.

11. A controller for automated age detection within a patient monitoring device, the controller comprising:
- an electrocardiogram feature calculator configured to calculate at least two electrocardiogram features from an electrocardiogram measurement of at least one heartbeat of a patient; and
- a patient classifier configured to classify the patient as an adult patient or a pediatric patient based on a regression analysis of a summation of the at least two electrocardiogram features calculated by the electrocardiogram feature calculator.

12. The controller of claim 11, wherein the patient classifier applies a logistic regression to the at least two electrocardiogram features for classifying the patient.

13. The controller of claim 11, further comprising:
a pediatric age estimator configured to estimate an age of a patient responsive to a classification of the patient as an pediatric patient.

14. The controller of claim 13, wherein the pediatric age estimator applies a linear regression to the at least two electrocardiogram features for estimating the age of the patient.

15. The controller of claim 11, wherein the at least two electrocardiogram features includes at least two of: a patient heart rate;
a T-wave amplitude relative to a QRS amplitude;
a QRS peak-to-peak amplitude;
a biphasic QRS complex;
a QRS duration; and
at least one negative T-wave.

16. A method of automated age detection for a patient monitoring device, the method comprising:
- the patient monitoring device calculating at least two electrocardiogram features from an electrocardiogram measurement of at least one heartbeat of a patient; and
- the patient monitoring device classifying the patient as an adult patient or a pediatric patient based on a regression analysis of a summation of the at least two electrocardiogram features.

17. The method of claim 16, wherein the patient monitoring device applies a logistic regression to the at least two electrocardiogram features for classifying the patient.

18. The method of claim 16, further comprising:
the patient monitoring device estimating an age of a patient responsive to the classification of the patient as a pediatric patient.

19. The method of claim 18, wherein the patient monitoring device applies a linear regression to the at least two electrocardiogram features for estimating the age of the patient.

20. The method of claim 18, further comprising:
the patient monitoring device applying one of an adult analysis or a pediatric analysis of the electrical activity of the heart responsive to the classification of the patient.

* * * * *